(12) United States Patent
Wekell et al.

(10) Patent No.: US 7,704,212 B2
(45) Date of Patent: Apr. 27, 2010

(54) REUSABLE INVASIVE FLUID PRESSURE MONITORING APPARATUS AND METHOD

(75) Inventors: William Wekell, Bellevue, WA (US); Joseph Basta, Duvall, WA (US)

(73) Assignee: Spacelabs Healthcare, Issaquah, WA (US)

( * ) Notice: Subject to any disclaimer, the term of this patent is extended or adjusted under 35 U.S.C. 154(b) by 162 days.

(21) Appl. No.: 11/454,105

(22) Filed: Jun. 14, 2006

(65) Prior Publication Data
US 2007/0293786 A1    Dec. 20, 2007

(51) Int. Cl.
*A61B 5/02* (2006.01)

(52) U.S. Cl. .................. 600/488; 600/485; 600/486; 600/561

(58) Field of Classification Search ............... 600/485, 600/486, 488, 561
See application file for complete search history.

(56) References Cited

U.S. PATENT DOCUMENTS

| 3,565,056 | A | * | 2/1971 | Statham ................. 600/561 |
| 4,243,201 | A | * | 1/1981 | Speidel ................. 251/297 |
| 4,341,224 | A | * | 7/1982 | Stevens ................. 600/488 |
| 4,539,998 | A | * | 9/1985 | McCord et al. .......... 600/488 |
| 4,576,181 | A | * | 3/1986 | Wallace et al. ......... 600/488 |
| 5,551,300 | A | * | 9/1996 | Vurek et al. ............. 73/706 |
| 5,752,918 | A | * | 5/1998 | Fowler et al. .......... 600/488 |
| 5,758,657 | A | * | 6/1998 | MacEachern ............ 600/486 |

* cited by examiner

*Primary Examiner*—Patricia C Mallari
(74) *Attorney, Agent, or Firm*—PatentMetrix

(57) ABSTRACT

The present invention is an apparatus and method for invasive bodily fluid pressure measurements using a pressure sensing assembly that is partially reusable. An embodiment includes a system for measuring a bodily pressure level having a support structure that includes at least one reusable pressure transducer that has a sensing face positioned on an exterior portion of the support structure, and a disposable pressure plenum having an inlet in fluid communication with a selected location within the body of a living being that is configured to be removably and slidably engaged with the support structure.

20 Claims, 5 Drawing Sheets

US 7,704,212 B2

REUSABLE INVASIVE FLUID PRESSURE MONITORING APPARATUS AND METHOD

TECHNICAL FIELD

The present invention relates generally to patient monitoring devices for medical use. In particular, the invention is an apparatus and method for invasive bodily fluid pressure measurements using a pressure sensing assembly that is partially reusable.

BACKGROUND OF THE INVENTION

Certain medical procedures require a bodily fluid pressure to be measured and monitored. For example, it is often desirable to measure and monitor an amniotic fluid pressure in a neonatal procedure, or to measure and monitor a pressure of an intracranial fluid in a neurological procedure. Most commonly, it is desirable to measure and monitor a blood pressure at a selected internal location in a patient. For example, in order to monitor the heart function in a patient, it is often advantageous to measure and monitor the blood pressure within the chambers of the heart. In all of the foregoing examples, the bodily fluid pressure is measured and monitored with a medical pressure transducer that is generally spaced apart from the body of the patient and fluidly coupled to a selected location in the patient's body by a catheter that is introduced into the body and positioned in a bodily region of interest. The fluid pressure in the selected region is then communicated to the medical transducer through the catheter.

In general, to measure and monitor a selected bodily pressure, the catheter is first filled with a sterile saline solution and de-bubbled. A hypodermic needle is then inserted into a selected portion of the body, such as a blood vessel. The catheter is then threaded through the hypodermic needle and directed into the body until the tip of the catheter is positioned at a location where the bodily pressure measurement is desired. When the catheter is suitably positioned, the needle may be removed, and the opening may be taped to secure the catheter tip at the selected location. The opposing end of the catheter is coupled to pressure tubing that is also similarly filled with a saline solution, which is then coupled to the pressure transducer. The pressure transducer may also be coupled to an external monitoring device and/or other devices, such as a visual display that permits the bodily pressure waveform of the patient to be viewed directly.

In the foregoing description, it is apparent that the various components of the bodily pressure measurement apparatus are exposed to the bodily fluid of the patient. Heightened concerns relating to the transmission of blood-borne pathogens, including hepatitis B virus (HBV) and the human immunodeficiency virus (HIV) have spurred the development of medical instruments, devices, and other items that are disposable to minimize the likelihood of transmitting infectious diseases between patients. Accordingly, disposable devices that are configured to measure and/or monitor a bodily pressure have been developed. Such disposable devices typically include a pressure sensor having an attached electrical cable, and an attached plastic housing that includes a valve device and associated tubing, which are generally fabricated as a single unit and provided to a medical provider as a single unit in a sterile package. Since a disposable pressure sensing assembly is intended to be used to measure and/or monitor a bodily pressure in a single patient and discarded afterwards, the cost associated with the use of such disposable assemblies may be relatively high. In particular, the pressure transducer and the associated electrical cable generally constitute the most costly components of the disposable assembly.

What is needed is a pressure sensing assembly for use in a patient monitoring system having a disposable first portion that is exposed to the patient-contacting fluid path, and a reusable second portion that remains isolated from the patient-contacting fluid path that includes the relatively costly components, such as the pressure transducer and the associated electrical cable.

SUMMARY OF THE INVENTION

The present invention relates generally to an apparatus and method for invasive bodily fluid pressure measurements using a pressure sensing assembly that is partially reusable. In one aspect, a system for measuring a bodily pressure level includes a support structure having at least one reusable pressure transducer that has a sensing face positioned on an exterior portion of the support structure, and a disposable pressure plenum having an inlet in fluid communication with a selected location within the body of a living being that is configured to be removably and slidably engaged with the support structure. The plenum includes a pressure compliant surface positioned in a corresponding relationship with the sensing face when the structure and the plenum are in engagement. In another aspect, an apparatus for monitoring a bodily fluid pressure in a patient includes a reusable support including at least one engagement location, and a pressure transducer disposed in the at least one engagement location and configured to produce electrical signals proportional to the bodily fluid pressure. The apparatus further includes a disposable plenum coupled to the bodily fluid pressure that forms at least a portion of a fluid path extending from the patient to the plenum. The plenum is removably and slidably securable to the at least one engagement location and fluidly isolates the fluid path from the at least one engagement location when the plenum is secured to the engagement location. In still another aspect, a method of measuring a selected bodily pressure in a patient is disclosed that includes providing a support that includes at least one reusable pressure sensor configured to measure the bodily pressure and having an exposed pressure sensing surface, slidably securing a disposable pressure plenum to the support, the disposable pressure plenum having a pressure compliant surface disposed thereon, fluidly coupling the plenum to a selected location within the patient, and measuring a bodily pressure at the selected location.

DETAILED DESCRIPTION OF THE EMBODIMENTS

The present invention is generally directed to an apparatus and method for invasive bodily fluid pressure measurements using a pressure sensing assembly that is partially reusable. Many of the specific details of certain embodiments of the invention are set forth in the following description and in FIGS. 1 through 5 to provide a thorough understanding of such embodiments. One skilled in the art will understand, however, that the present invention may have additional embodiments, or that the present invention may be practiced without several of the details described in the following description.

Figure 1:
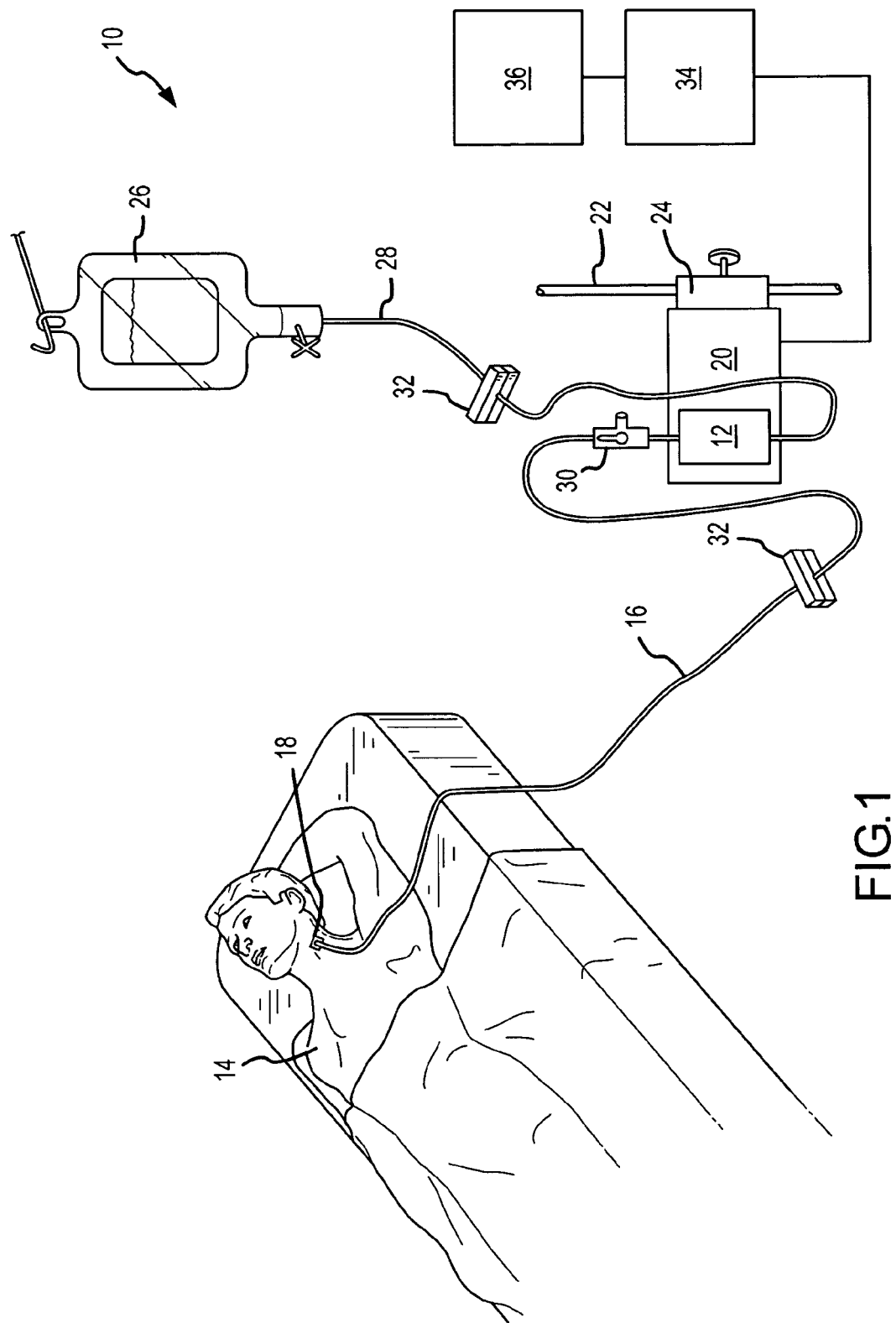
FIG. 1 is an isometric view of a patient monitoring system according to an embodiment of the invention.

FIG. 1 is an isometric view of a patient monitoring system 10 according to an embodiment of the invention. The system 10 includes a pressure plenum 12 coupled to a pressure tube 16 that extends from the plenum 12 through a flow valve 30 to an end of a catheter 18. An apical tip (not shown) of the catheter 18 is inserted into the patient 14 and extends into the body of the patient 14 to a desired location. The system 10 also includes a transducer support 20 that includes at least one pressure transducer (not shown) that is positioned in an abutting relationship with the plenum 12, and further removably supports the plenum 12. Accordingly, the transducer support 20 is capable of measuring and monitoring a bodily pressure transmitted to the plenum 12 through the tube 16 from a selected position in the body of the patient 14. The transducer support 20 will be described in further detail below. Although FIG. 1 shows a single plenum 12 positioned on the transducer support 20, one skilled in the art will readily understand that more than one pressure plenum 12 may be positioned on the transducer support 20 and coupled to other selected pressure transducers positioned within the support 20 to permit other pressure measurement locations within the body of the patient 14 to be simultaneously monitored. The transducer support 20 may be supported on a vertical support column 22 and held at a preferred vertical elevation relative to the patient 14 by a clamp 24 that is vertically positionable on the support column 22. The pressure plenum 12 may also be coupled to a saline bag 26 positioned generally at an elevation above the plenum 12 through a saline tube 28 to allow the pressure tube 16 and the catheter 18 to be purged with a saline solution retained by the saline bag 26. Line restrictors 32 positioned on the saline tube 28 and the pressure tube 16 may also be present to assist in the purging process. The support 20 may be electrically coupled to a processor 34 operable to process signals received from the pressure transducer positioned within the support 20 and to generate a visual image of a monitored pressure level for display on a visual display device 36.

Figure 2:
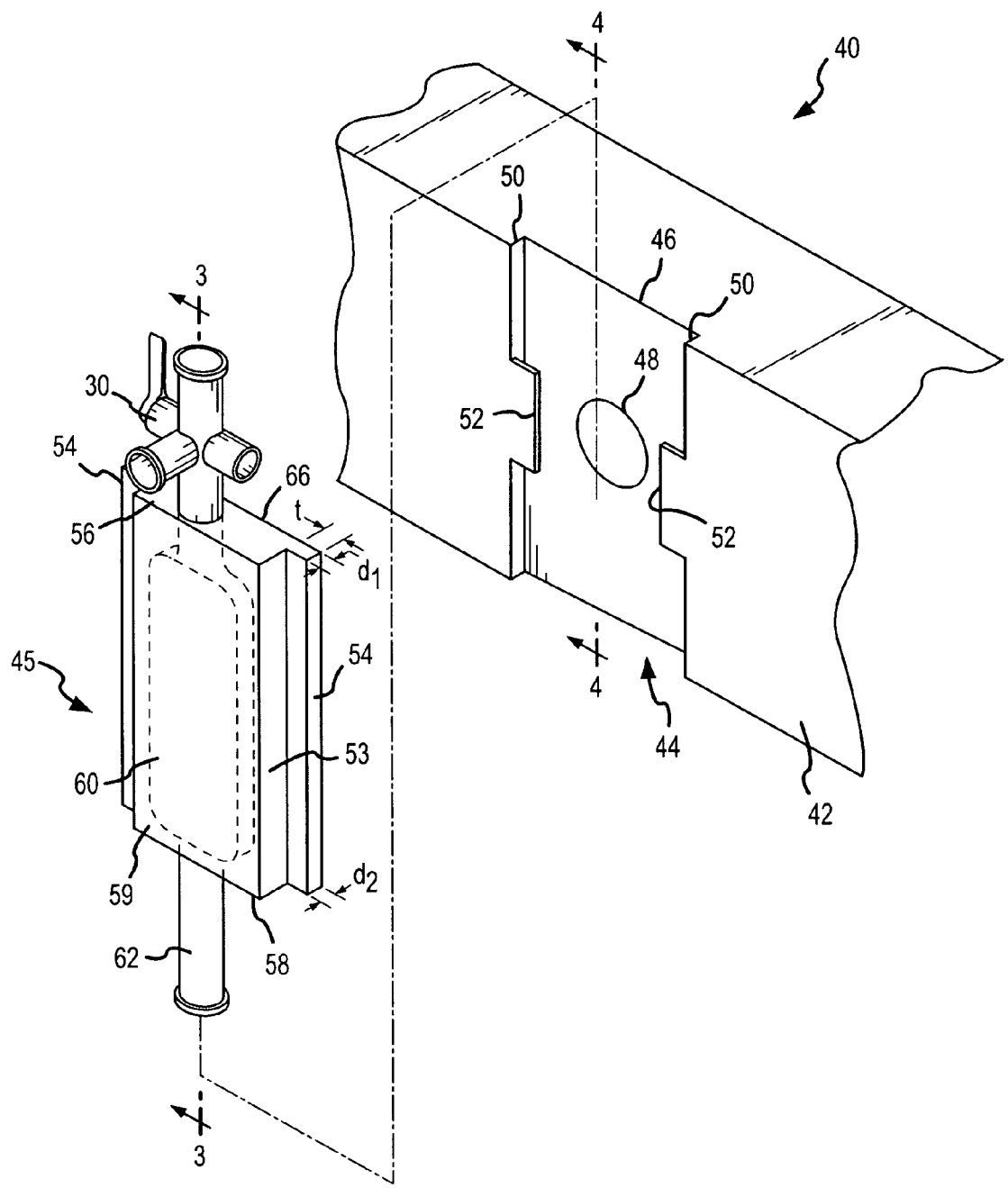
FIG. 2 is a partial isometric view a patient monitoring system according to another embodiment of the invention.

FIG. 2 is a partial isometric view of a patient monitoring system 40 according to another embodiment of the invention. The system 40 includes a transducer support 42 that includes at least one slot 44 that is configured to slidably or otherwise receive a pressure plenum 45. The slot 44 includes a planar floor 46 that has a pressure-sensing diaphragm 48 of a pressure transducer located thereon. The slot 44 also includes a pair of opposed sidewalls 50 that extend outwardly from the floor 46 and are spaced apart to permit the plenum 45 to be received between the side walls 50. A pair of retainers 52 extend inwardly from the side walls 50 to retain the plenum 45 in position when the plenum 45 is mounted on the support 42.

Still referring to FIG. 2, the plenum 45 includes an inner face 66 that is configured to abut the floor 46 of the slot 44, and an opposing outer wall 59 that is sealably coupled to the inner face 66 by opposing longitudinal sides 53, a first end 56 and a second end 58 to form an internal pressure chamber 60. The first end 56 of the plenum 45 may be coupled to the flow valve 30 to permit fluid communication with the internal pressure chamber 60, while the second end 58 may also include a suitable coupling 62 to permit the saline tube 28 of FIG. 1 to fluidly communicate with the pressure chamber 60. Although FIG. 2 does not show the pressure tube 16 and the saline tube 28, it is understood that the pressure tube 16 and/or the saline tube 28 may be combined with the plenum 45 form an integral assembly that may be supplied to a medical provider as a single unit.

The opposing longitudinal sides 53 of the plenum 45 further include a pair of lugs 54 that extend outwardly from the sides 53 of the plenum 45. The lugs 54 are configured to extend outwardly from the sides 53 by a relatively constant distance "t" and also taper from a first depth "$d_1$" at the first end 56 of the plenum 45 to a second depth "$d_2$" at the second end 58 of the plenum 45. The first depth "$d_1$" is suitably dimensioned to allow the lugs 54 to pass between inner surfaces of the retainers 52 and the floor 46, while the second depth "$d_2$" is dimensioned so that the lugs 54 cannot pass between the inner surfaces of the retainers 52 and the floor 46. Accordingly, when the plenum 45 is inserted between the side walls 50, an interference fit is established between the generally tapered lugs 54 and the inner surfaces of the retainers 52.

Figure 3:
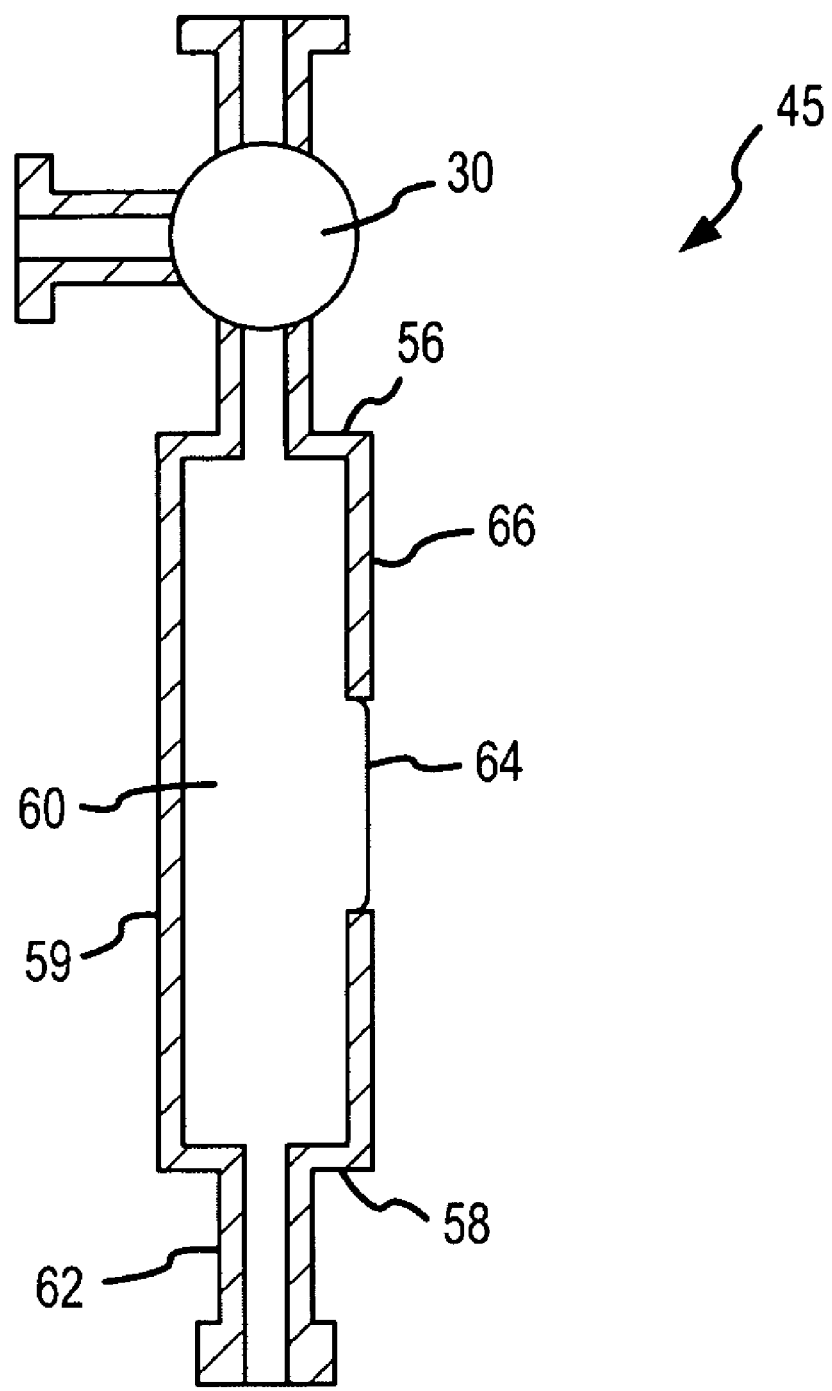
FIG. 3 is a cross-sectional view of the pressure plenum of FIG. 2.

Referring briefly now to FIG. 3, a cross-sectional view of the pressure plenum 45 along an axis "3-3" of FIG. 2 is shown. The inner face 66 of the plenum 45 includes a membrane 64 that is structured to have a confronting and pressure communicating relationship with the diaphragm 48 shown in FIG. 2 when the plenum 45 is mounted on the transducer support 42. Accordingly, it is understood that the membrane 64 is relatively thin in cross-section when compared to the cross-sectional thicknesses of other portions of the plenum 45 so that variations in fluid pressure in the chamber 60 will result in resolvable deflections in the membrane 64 while causing relatively insignificant deflections in the other portions of the plenum 45. The plenum 45 may thus be formed from any relatively rigid polymeric material suitable for use in medical devices, while the membrane 64 may be comprised of any relatively flexible material that is similarly suited for use in medical devices. For example, a thin film of a silicone elastomer, such as SILASTIC silicone rubber, available from the Dow-Corning Corporation of Midland, Mich., may be used to fabricate the membrane 64. Alternately, a polyurethane or a polypropylene material may be used, although still other suitable materials are known in the art.

Figure 4:
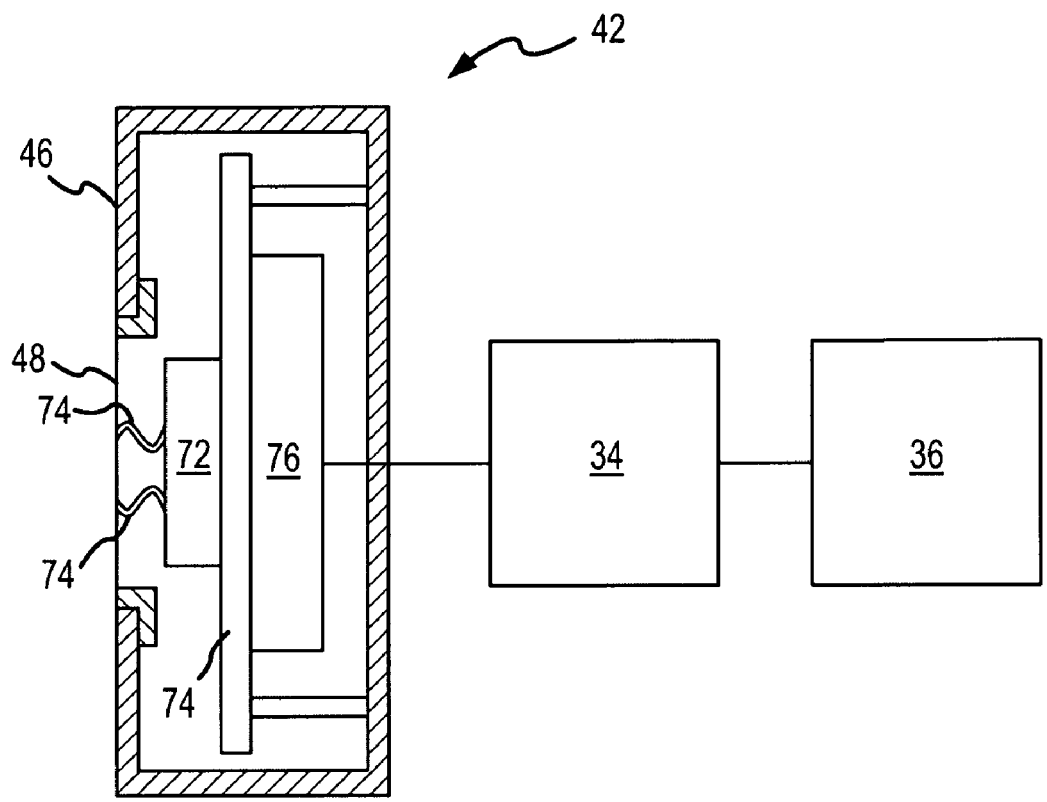
FIG. 4 is a cross-sectional and diagrammatic view of the transducer support of FIG. 2.

FIG. 4 is a cross-sectional and diagrammatic view of the transducer support 42 of FIG. 2 viewed along the section line "4-4" of FIG. 2. The transducer support 42 includes a pressure transducer 72 that is coupled to the diaphragm 48. In one particular embodiment, the transducer 72 includes a resistance bridge network that is formed on the diaphragm 48 that is coupled to the transducer 72 by lead wires 74. In another particular embodiment, the transducer 72 is a capacitive-type device, wherein the diaphragm 48 comprises a first plate of the capacitor. In still another particular embodiment the transducer 72 may be a piezoelectric type, wherein the diaphragm is mechanically coupled to a piezoelectric element so that pressures acting on the diaphragm 48 may deform the piezoelectric element. Alternately, and in still another particular embodiment, the pressure transducer 72 may be replaced with a force transducer that is coupled to the diaphragm 48 by a connecting member that is configured to transmit a force from the diaphragm 48 to the force transducer. Accordingly, when a pressure acts on the diaphragm 48, displacements of the diaphragm 48 may be transferred to the force transducer through the connecting member.

Still referring to FIG. 4, the transducer support 42 may also include an electronics package 76 that is supported on a printed circuit board (PCB) 74 positioned and supported within an interior portion of the transducer support 42. The electronics package 76 may include circuits directed to various signal processing functions. For example, the package 76 may include circuits directed to converting analog signals received from the transducer 72 into signals that correspond to an appropriate pressure measurement scale. For example, the signals received from the transducer 72 may be converted by the package 76 to correspond to a pressure value in inches of mercury (in. Hg). The package 76 may also include circuits directed to the comparison of a measured bodily pressure level with a pre-selected alarm level, so that an alarm status is generated if the detected pressure rises above, or alternately falls below a specified level. Still other circuits residing in the package 76 may include an analog-to-digital (A/D) converter that receives an analog signal from the transducer 72 and converts the signal to a digital signal.

The package 76 may also be coupled to the processor 34 by a suitable signal line to permit the processor 34 to further process and/or store pressure values measured by the transducer 72. The processor 34 may be coupled to the display 36 so that the measured pressure values may be conveniently viewed. Although FIG. 4 shows the package 76 coupled to the processor 34, it is understood that the package 76 may include many, if not all of the circuits required to perform the desired signal processing. Accordingly, in certain instances, the package 76 may be coupled directly to the display 36. Moreover, the package 76 may also include circuits that permit measured pressure levels to be wirelessly communicated to other external devices, such as a central processing and storage device, as is well-known in the art.

Referring again to FIG. 2, the operation of the patient monitoring system 40 will now be described. When it is desired to measure and/or monitor a selected bodily pressure, a suitable slot 44 is identified on the transducer support 42. As briefly described earlier, the support 42 may have more than one slot 44 so that different pressure ranges may be accommodated by the various pressure sensing diaphragms 48 located on the transducer support 42. For example, a selected one of the slots 44 may be dedicated to measuring and/or monitoring an arterial pressure, while another selected one may be dedicated to the measurement of an inter-cranial pressure. In any case, the appropriate plenum 45 is positioned in the selected slot 44 by positioning the plenum 45 adjacent to the slot 44 and aligning the plenum 45 between the sidewalls 50. The plenum 45 is then slidably urged into the slot 44 so that the lugs 54 of the plenum 45 engage the retainers 52. When the lugs 54 fully engage the retainers 52, a predetermined interference fit exists between the retainers 52 and the lugs 54 so that a manually-applied force does not result in further sliding movement of the plenum 45 relative to the slot 44. At this point, the membrane 64 of FIG. 3 will be properly positioned on the diaphragm 48. The saline tube 28 and the pressure tube 16 of FIG. 1 may then be coupled to the plenum 45 and the system 40 may be de-bubbled prior to the insertion of the catheter 18 into the patient 14.

Figure 5:
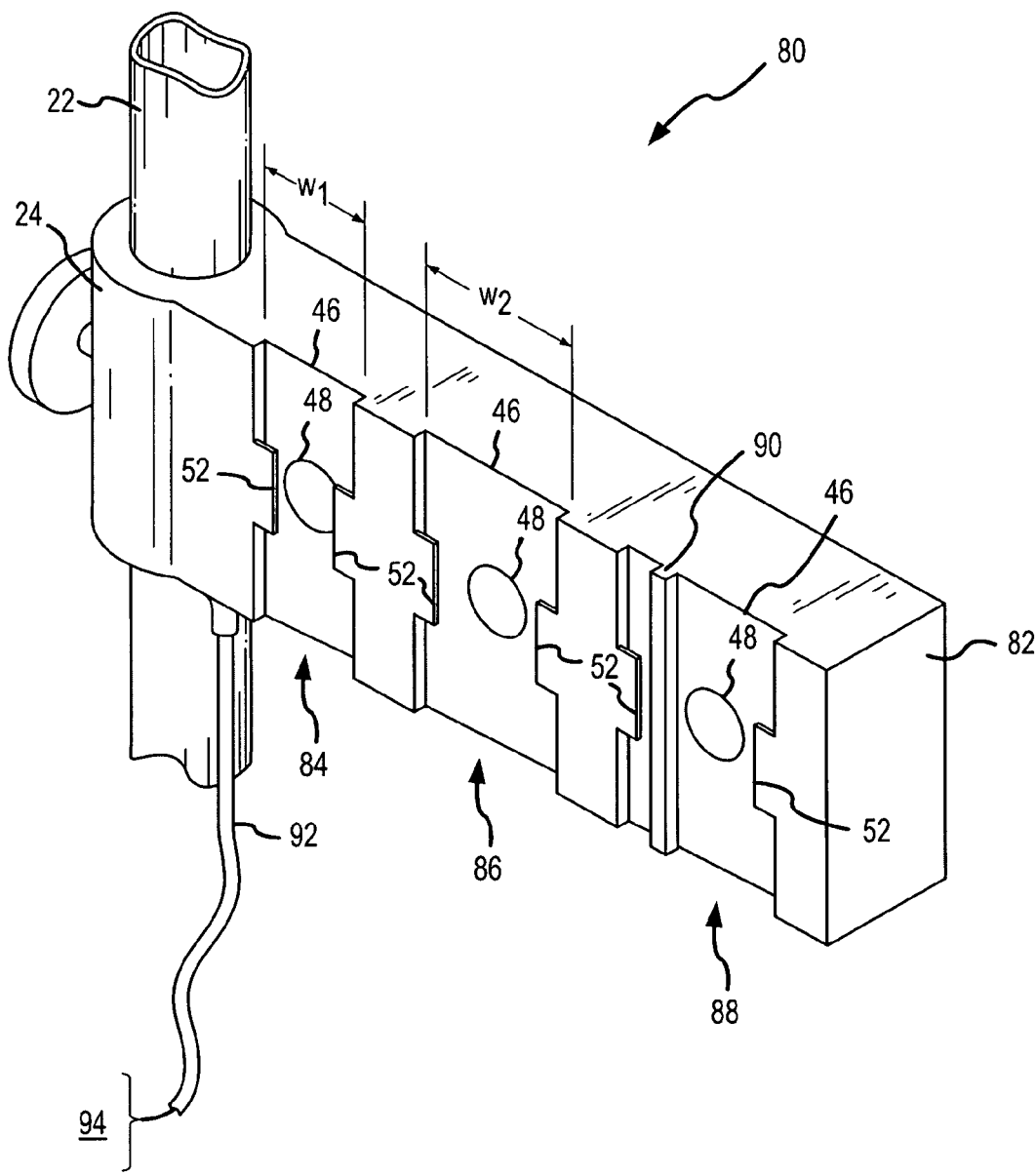
FIG. 5 is a partial isometric view of a patient monitoring system according to another embodiment of the invention.

FIG. 5 is a partial isometric view of a patient monitoring system 80 according to another embodiment of the invention. Many of the details shown in FIG. 5 have been described previously, and in the interest of brevity, will not be described further. The patient monitoring system 80 includes a transducer mount 82 having a first slot 84 configured with a first width "$w_1$" that accommodates a first plenum (not shown) that is dedicated to measuring a first bodily pressure in the patient 14 (FIG. 1). The transducer mount 82 also includes a second slot 86 that is configured with a second slot width "$w_2$" that is different from the first slot width "$w_1$". The second slot 86 similarly accommodates a second plenum (also not shown) that is dedicated to the measurement of a second bodily pressure. Still other slots may be provided on the transducer mount 82 that are configured to accommodate other pressure plenums. For example, the slot 88 includes a ridge 90 that extends along the length of the floor 46 of the slot 88 that is positioned within a corresponding groove formed in a plenum (not shown). Since the slot 84 and the slot 86 are configured to accommodate plenums having a corresponding width, the possibility of positioning a plenum that is in fluid communication with a selected bodily fluid pressure adjacent to a transducer in the support 82 that is intended to measure a different bodily fluid pressure is greatly minimized, since interchangeability is eliminated. One skilled in the art will similarly recognize that the slot 88 having the ridge 90 also prevents a plenum in fluid communication with a bodily fluid pressure from being mis-positioned on the support 82 by restricting the slot to accommodate only a properly configured plenum Still referring to FIG. 5, the transducer mount 82 may also include an electrical cable 92 that is coupled to the electronic package contained within the transducer mount 82. The cable 92 may be structured to transmit data from the mount 82 to other external devices, as previously described. Accordingly, the cable 92 may include a plurality of conductors that comprise a parallel data line. Alternately, the, cable may include shielded conductors operable to transmit an analog signal to other external devices 94. In other aspects, the cable 92 may be configured to couple to a universal serial bus (USB) port that permits the transducer mount 82 to communicate with other external devices.

The foregoing embodiments provide numerous advantages over the prior art. For example, since the plenum is fluidly isolated and separable from the pressure transducer, the plenum may be discarded after use by a single patient, thus reducing the possibility of transmitting blood-borne pathogens to other patients. Additionally, since the plenum comprises a relatively inexpensive portion of the disclosed pressure monitoring system, the plenum may be discarded with minimal economic effect on health care costs. The foregoing embodiments also advantageously eliminate electrical connection problems associated with many prior art devices by eliminating the electrical cable associated with individual pressure transducers. Instead, pressure signals from the one or more pressure transducers positioned within the disclosed transducer support are communicated to a processor within a single cable, or in a particular embodiment, by wireless means Still other advantages are present in the foregoing embodiments. For example, by providing slots for the plenums having different geometrical configurations, interchangeability of plenums with slots in the transducer support is eliminated, thus affording protection against mis-positioning a plenum adjacent to a pressure transducer not intended to receive pressure information from the plenum.

Although the foregoing has discussed pressure measurement within the specific context of invasive blood pressure measurement, it is understood that the foregoing is also applicable to pressure measurements in other regions of the body. For example, the various embodiments of the present invention may, without significant modification, be used to measure and monitor the intracranial pressure in a patient. Additionally, from the foregoing it will be appreciated that, although specific embodiments of the invention have been described herein for purposes of illustration, various modifications may be made without deviating from the spirit and scope of the invention. For example, certain features shown in the context of one embodiment of the invention may be incorporated in other embodiments as well. Accordingly, the invention is not limited by the foregoing description of embodiments except as by the following claims.

What is claimed is:

1. A monitoring system for measuring a pressure level at a plurality of selected locations within a living body, comprising:
   a first support structure and a second support structure physically connected to each other, wherein each support structure comprises:
   a) a recess, wherein said recess is defined by a floor and opposing sidewalls, each of said sidewalls having a retainer, wherein each retainer is spaced apart from said floor by a tapered space, and wherein the depth of the tapered space of the first support structure is different than the depth of the tapered space of the second support structure;
   b) at least one reusable transducer having a sensing face disposed on an exterior portion of the support structure, the sensing face positioned within the recess, and
   a first disposable pressure plenum and a second disposable pressure plenum, wherein each disposable pressure plenum comprises:
   a) an inlet configured to be placed in fluid communication with one of said plurality of selected locations,
   b) opposing sides, each of said opposing sides including a lug, wherein each lug has a tapered depth, wherein the tapered depth of the first disposable pressure plenum fits the tapered space of the first support structure, wherein the tapered depth of the second disposable pressure plenum fits the tapered space of the second support structure, and wherein each of said plenums removably engages the first or second support structures by sliding the lug into the tapered space defined by the retainer and floor of said first or second support structures; and
   c) a pressure compliant surface positioned in a corresponding relationship with the sensing face when the support structure and the disposable pressure plenum are in engagement.

2. The monitoring system of claim 1, wherein each of the disposable plenums comprises a relatively rigid polymeric structure having a compliant membrane that confronts the sensing face when the plenum and the support structure are in engagement.

3. The monitoring system of claim 2, further comprising a catheter having an apical portion configured to be positioned at least one of the selected locations that is operable to communicate a pressure from the selected location to the disposable plenum.

4. The monitoring system of claim 3, further comprising a pressure tube fluidly coupled to a distal portion of the catheter and fluidly coupled to the disposable plenum.

5. The monitoring system of claim 4, further comprising a saline source fluidly coupled to the disposable plenum and operable to supply a saline solution to the catheter and the pressure tube.

6. The monitoring system of claim 1, further comprising a processor coupled to at least one of the support structures, the processor operable to receive input signals from the at least one reusable transducer and to generate visual image signals therefrom for display on a visual display device coupled to the processor.

7. The monitoring system of claim 1, wherein at least one of the support structures is adjustably positionable at a selected elevation relative to the living body.

8. The monitoring system of claim 1, wherein the at least one reusable transducer comprises a pressure transducer.

9. The monitoring system of claim 1, wherein the at least one reusable transducer comprises a force transducer.

10. An apparatus for monitoring a plurality of fluid pressures in a patient, comprising:
    a first reusable support including a first engagement location physically connected to a second reusable support including a second engagement location, wherein each of said first and second engagement locations comprises a slot defined by a floor, opposing sidewalls, and retainers on each of the opposing sidewalls, wherein each retainer is spaced apart from said floor by a tapered space, and wherein the depth of the tapered space of the first reusable support is different than the depth of the tapered space of the second reusable support;
    a transducer disposed in each of said engagement locations and configured to produce electrical signals proportional to at least one of the fluid pressures;
    a first disposable plenum operable to be coupled to at least one of the fluid pressures and forming at least a portion of a fluid path extending from the patient to the first disposable plenum, the first disposable plenum being removably securable to the first engagement location and fluidly isolating the fluid path from the first engagement location when the first disposable plenum is secured to the first engagement location, wherein the first disposable plenum has opposing sides, each of said opposing sides including a lug, wherein each lug has a tapered depth, wherein the tapered depth of the first disposable plenum fits the tapered space of the first reusable support; and
    a second disposable plenum operable to be coupled to at least one of the fluid pressures and forming at least a portion of a fluid path extending from the patient to the second disposable plenum, the second disposable plenum being removably securable to the second engagement location and fluidly isolating the fluid path from the second engagement location when the second disposable plenum is secured to the second engagement location, wherein the second disposable plenum has opposing sides, each of said opposing sides including a lug, wherein each lug has a tapered depth, wherein the tapered depth of the second disposable plenum fits the tapered space of the second reusable support.

11. The apparatus of claim 10, wherein at least one of the disposable plenums further comprises a flow valve coupled to a pressure tube configured to be coupled to a catheter extending into the patient.

12. The apparatus of claim 10, wherein at least one of the disposable plenums further comprises a saline tube that is configured to be coupled to a source of a saline solution.

13. The apparatus of claim 10, wherein at least one of the disposable plenums further comprises a pressure compliant membrane disposed in a wall of the plenum, and the plenum is further configured to position the pressure compliant membrane adjacent to the transducer when the plenum is secured to the engagement location.

14. The apparatus of claim 10, wherein at least one of the supports further comprises an electronics package positioned within an interior portion of the support, the electronics package receiving signals from the transducer and transferring the signals to an external processor.

15. The apparatus of claim 14, wherein the electronics package and the external processor are coupled by a conductive line extending from the package to the processor.

16. The apparatus of claim 14, wherein the electronics package and the external processor are wirelessly coupled.

17. The apparatus of claim 14, further comprising a visual display device coupled to the processor.

18. The apparatus of claim 10, wherein at least one of the supports further comprises an electronics package positioned with an interior portion of the support, the electronics package receiving signals from the transducer and processing the signals to produce data suitable for transmission to a visual display.

19. The apparatus of claim 10, wherein the transducer further comprises at least one of a resistive bridge-type pressure transducer, a capacitive-type pressure transducer and piezoelectric-type pressure transducer.

20. The apparatus of claim 10, wherein the transducer further comprises a force transducer coupled to a diaphragm by a connecting member.

* * * * *